United States Patent

Nasuno et al.

Patent Number: 5,468,878
Date of Patent: Nov. 21, 1995

[54] CYCLOHEXANEDIONE DERIVATIVES

[75] Inventors: Ichiro Nasuno; Mitsuru Shibata; Masashi Sakamoto; Kazuyoshi Koike, all of Sodegaura, Japan

[73] Assignee: Idemitsu Kosan Co., Ltd., Tokyo, Japan

[21] Appl. No.: 379,642

[22] PCT Filed: Oct. 8, 1993

[86] PCT No.: PCT/JP93/01453
§ 371 Date: Feb. 2, 1995
§ 102(e) Date: Feb. 2, 1995

[87] PCT Pub. No.: WO94/08988
PCT Pub. Date: Apr. 28, 1994

[30] Foreign Application Priority Data

Oct. 15, 1992 [JP] Japan ................. 4-277186
Dec. 4, 1992 [JP] Japan ................. 4-325727

[51] Int. Cl.⁶ .................. C07D 335/06; C07D 311/08; A01N 43/18
[52] U.S. Cl. .................. 549/23; 549/28; 549/404; 549/405; 504/288; 504/292; 504/298
[58] Field of Search .................. 549/23, 28, 404, 549/405; 504/288, 292, 298; 564/256

[56] References Cited

U.S. PATENT DOCUMENTS

| | | | |
|---|---|---|---|
| 4,511,391 | 4/1995 | Serban et al. | 504/288 |
| 4,585,786 | 4/1986 | Berthelon | 549/23 |
| 4,741,755 | 5/1988 | Knudsen et al. | 504/288 |
| 4,780,127 | 10/1988 | Michaely et al. | 71/103 |
| 4,812,160 | 3/1989 | Jahn et al. | 504/292 |
| 4,895,868 | 1/1990 | Chandraratna | 549/23 |
| 4,937,386 | 6/1990 | Cleda et al. | 568/31 |
| 4,954,165 | 9/1990 | Baba et al. | 71/103 |
| 5,092,919 | 3/1992 | Nguyen | 71/122 |
| 5,114,461 | 5/1992 | Geach et al. | 71/88 |
| 5,132,434 | 7/1992 | Watanabe et al. | 504/288 |

FOREIGN PATENT DOCUMENTS

| | | |
|---|---|---|
| 0053981 | 3/1987 | Japan. |
| 2120247 | 11/1983 | United Kingdom. |
| 9404524 | 3/1994 | WIPO. |
| 9408988 | 4/1994 | WIPO. |

Primary Examiner—Richard L. Raymond
Assistant Examiner—Deborah Lambkin
Attorney, Agent, or Firm—Frishauf, Holtz, Goodman, Langer & Chick

[57] ABSTRACT

Cyclohexanedione derivatives of the general formula (I),

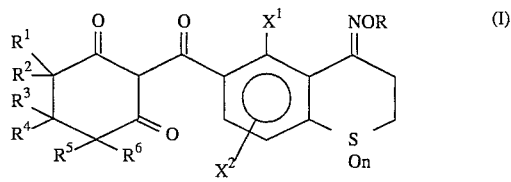

wherein:
R is a $C_1$-$C_4$ alkyl group,
each of $R^1$ to $R^6$ is independently hydrogen or a $C_1$-$C_4$ alkyl group,
$X^1$ is a $C_1$-$C_4$ alkyl group,
$X^2$ is hydrogen or a $C_1$-$C_4$ alkyl group, and
n is an integer of 0 to 2.
or salts thereof exhibit high selectivity for corn, wheat and barley, can control gramineous weeds and broad-leaved weeds at a low dosage, and can be desirably used as an active ingredient of a herbicide.

11 Claims, No Drawings

CYCLOHEXANEDIONE DERIVATIVES

This application is a 371 of PCT/JP93/01453 filed Oct. 8, 1993.

The present invention relates to cyclohexanedione derivatives which have herbicidal activity. More specifically it relates to novel cyclohexanedione derivatives and herbicides containing them as active ingredients.

TECHNICAL BACKGROUND

During a planting period of corn, etc., triazine-containing herbicides such as atrazine and acid anilide-containing herbicides such as alachlor and metolachlor have been conventionally used. However, atrazine shows low efficacy to gramineous weeds, while alachlor and metolachlor show low efficacy to broad-leaved weeds. It is therefore difficult at the present times to control both of gramineous weeds and broad-leaved weeds at once using a single herbicide. Further, the use of these chemicals in combination does not give any sufficient effect. Moreover, the above herbicides are undesirable in view of an environmental problem due to their high dosage requirement.

On the other hand, it is known that specific benzoylcyclohexanedione derivatives have herbicidal activity (see JP-B-1-30818, JP-A-61-155347, JP-A-1-143851, JP-A-3-120202, EP 135,191A, EP 186,118A, EP 186,119A, U.S. Pat. No. 4,954,165, GB 2,215,333A, EP 336,898A, U.S. Pat. No. 4,937,386, U.S. Pat. No. 4,780,127, U.S. Pat. No. 5,092,919 and PCT International Publication. 90/05712). Typical examples of the benzoylcyclohexanedione derivatives disclosed in the above Publications are as follows.

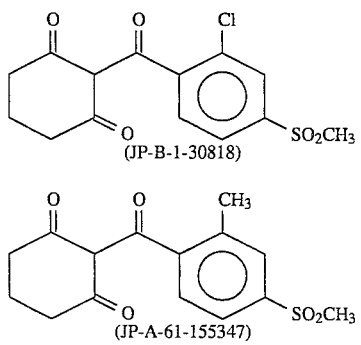

Further, JP-A-64-6256 discloses that cyclohexanedione derivatives having a fused bicyclic group containing heteroatoms exhibit herbicidal activity.

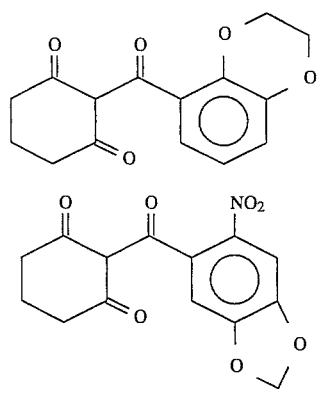

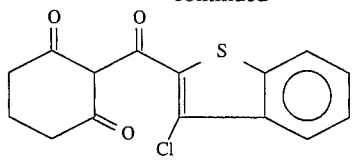

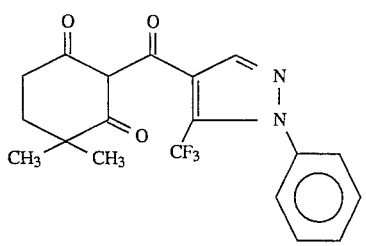

However, cyclohexanedione derivatives having a thiochroman ring such as compounds of the present invention are not known yet.

Further, the cyclohexanedione derivatives that have been already disclosed are insufficient in practical use, particularly poor in herbicidal activity to gramineous weeds such as barnyardgrass and green foxtail.

DISCLOSURE OF THE INVENTION

It is therefore a first object of the present invention to provide novel cyclohexanedione derivatives which exhibit high selectivity for corn, wheat and barley and can control both of gramineous weeds and broad-leaved weeds at low dosage.

It is a second object of the present invention to provide herbicides containing the above novel cyclohexanedione derivatives as active ingredients.

The novel cyclohexanedione derivatives of the present invention are compounds of the general formula (I).

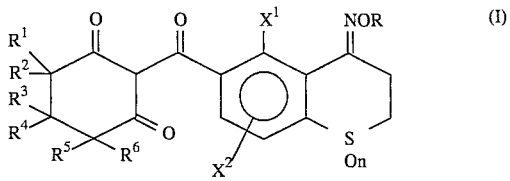

In the general formula (I), R is a $C_1$-$C_4$ alkyl group such as methyl, ethyl, propyl or butyl. The propyl and butyl may be linear or branched. R is preferably methyl or ethyl.

Each of $R^1$ to $R^6$ is independently hydrogen or a $C_1$-$C_4$ alkyl group such as methyl, ethyl, propyl or butyl. The propyl and butyl may be linear or branched. Each of $R^1$ to $R^6$ is preferably hydrogen or methyl.

$X^1$ is a $C_1$-$C_4$ alkyl group such as methyl, ethyl, propyl or butyl. The propyl and butyl may be linear or branched. $X^1$ is preferably methyl.

$X^2$ is hydrogen or a $C_1$-$C_4$ alkyl group such as those specified concerning the above $X^1$. $X^2$ is preferably hydrogen or methyl. When $X^2$ is a $C_1$-$C_4$ alkyl group, the position of its substitution is the 7- or 8-position of the thiochroman ring, preferably the 8-position.

n is the number of oxygen atom(s) bonding to the sulfur atom, and it is an integer of 0 to 2. When n=0, sulfide is represented, when n=1, sulfoxide is represented, and when n=2, sulfone is represented. n= 2 (sulfone) is preferred.

The cyclohexanedione derivatives of the general formula (I) have geometrical isomers with regard to the alkoxyimino group as shown below, and the cyclohexanedione derivatives of the present invention include these two isomers and a mixture of these isomers.

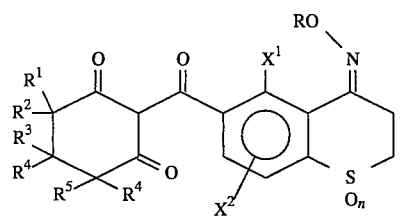

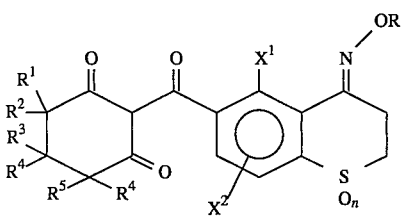

[wherein R, $R^1$ - $R^6$, $X^1$, $X^2$ and n are as defined above.]

Further, the cyclohexanedione derivatives of the general formula (I) can have the following tautomeric structures. The cyclohexanedione derivatives of the present invention include any one of compounds having these structures and a mixture of the compounds having these structures.

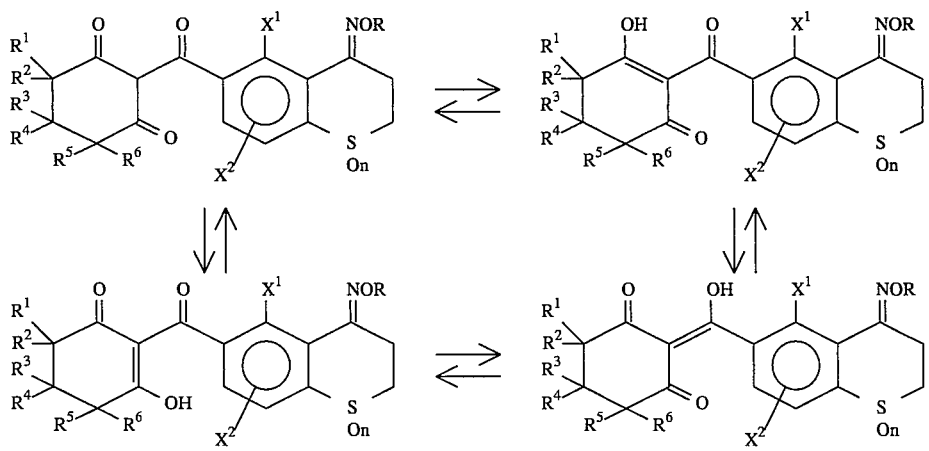

Further, the cyclohexanedione derivatives of the general formula (I) are acidic substances, and can be easily converted to salts by treating them with various bases. The cyclohexanedione derivatives of the present invention also include these salts.

The bases which form salts with the cyclohexanedione derivatives of tile present invention are not specially limited. Examples of the bases include known organic bases such as amines and anilines and known inorganic bases which can form sodium salts and potassium salts.

Examples of the amines include alkylamine, dialkylamine and trialkylamine. The alkyl group of these amines is generally a $C_1$-$C_4$ alkyl. Examples of the anilines include aniline, alkylaniline and dialkylaniline. The alkyl group of these anilines is generally a $C_1$-$C_4$ alkyl group.

Examples of the bases which can form sodium salts include sodium hydroxide and sodium carbonate, and examples of the bases which can form potassium salts include potassium hydroxide and potassium carbonate.

The method for the production of the cyclohexanedione derivatives of the general formula (I) will be explained hereinafter.

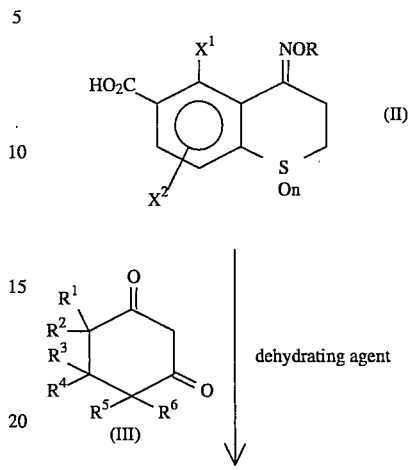

-continued

-continued

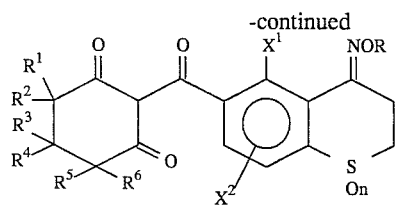
(I)

[wherein R, $R^1$ - $R^6$, $X^1$, $X^2$ and n are as defined above.]

That is, a compound of the general formula (II) is allowed to react with a compound of the general formula (III) in the presence of a dehydrating agent such as dicyclohexylcarbodiimide (hereinafter "DCC") or the like, and then the so-formed compound is subjected to a rearrangement reaction to form the intended cyclohexanedione derivative of the general formula (I). During the course of the above preparation, an ester compound of the general formula (IV) is formed. This compound can be isolated, while it is preferred to directly subject this compound to a rearrangement reaction without isolation.

The reaction solvent used for the condensation of the compound (II) and the compound (III) is not specially limited if it is inert to the reaction, while acetonitrile and tertiary amyl alcohol are preferred. The reaction temperature is not specially limited if it is in the range of from 0° C. to the boiling point of the solvent, while the temperature around room temperature is preferred. As the dehydrating agent, CDI (1,1-carbonyldiimidazole) or EDC (1-( 3-dimethylaminopropyl)-3-ethylcarbodiimide ) may be also used besides the above DCC. The reaction time for the condensation of the compound (II) and the compound (III) is 1 to 48 hours, while the reaction generally completes in about 8 hours.

The rearrangement reaction is attained by allowing cyanide ion to act on the compound (IV). The base used therefor includes sodium carbonate, potassium carbonate, triethylamine and pyridine. The base is used preferably in an amount of 1 to 2 mol equivalents based on the compound (IV). The cyanide which releases cyanide ion includes alkali metal cyanides and cyanohydrin compounds such as acetone cyanohydrin, and the cyanide is used in an amount of 0.05 to 0.5 mol equivalent based on the compound (IV). The rearrangement reaction can be smoothly proceeded with by adding a phase transfer catalyst such as crown ether compounds in the reaction mixture. The reaction temperature is not specially limited if it is in the range of from 0° C. to the boiling point of the solvent, while the temperature around room temperature is preferred. The rearrangement reaction is completed in 1 to 72 hours, while it generally finishes in about 8 hours.

The compound of the general formula (II) described as a starting material for the production of the cyclohexanediones of the general formula (I) can be easily produced by a combination of known synthesis methods. The reaction process for the production of the compound (II) is as shown below.

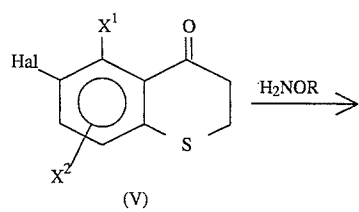
(V)

-continued

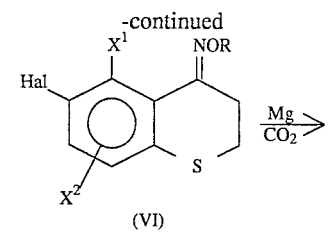
(VI)

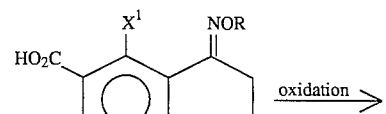
(IIa)

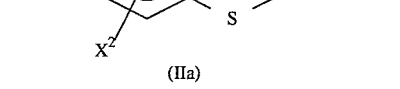
(IIb) or (IIc)

[wherein Hal is halogen and R, $X^1$, $X^2$ and n are as defined above.]

The ketone (V) as a starting material can be obtained by the method described in JP-A-58-198483 and International Publication WO88/06155.

The formation of an oxime from the ketone (V) is carried out by allowing the ketone (V) and alkoxyamine to react in water or an organic solvent (e.g., ethanol, methanol or acetic acid) in the presence of an acid catalyst (e.g., hydrochloric acid) or a basic catalyst (e.g., pyridine, aniline, sodium hydroxide or sodium carbonate) in the range of from 0° C. to the reflux temperature of the solvent. It is preferred to carry out tile reaction in ethanol in the presence of pyridine at the reflux temperature.

Then, the so-formed oxime (VI) is allowed to react with metal magnesium (Mg) to form a Grignard reagent, and the Grignard reagent is allowed to react with carbon dioxide to obtain carboxylic acid sulfide (IIa). The solvent is preferably selected from ethers such as diethyl ether and tetrahydrofuran.

The amount of the metal magnesium (Mg) used for obtaining the Grignard reagent is preferably 1.0 to 5.0 mol equivalent to the oxime of the formula (VI). The reaction for forming the Grignard reagent is preferably carried out in the presence of alkyl halide such as methyl iodide or ethyl bromide, since the reaction proceeds smoothly. The amount of the alkyl halide is preferably 0.1 to 3.0 mol equivalent to the oxime (VI).

The reaction between the Grignard reagent and carbon dioxide ($CO_2$) is carried out by blowing carbon dioxide gas from a cylinder, or by blowing carbon dioxide gas generated from dry ice (solid carbon dioxide), into the Grignard reagent in a solvent. The reaction may be carried out by directly adding dry ice into the Grignard reagent in the solvent.

An oxidizing agent (e.g., hydrogen peroxide, peracetic acid or sodium metaperiodate) is allowed to react on the above-obtained carboxylic acid sulfide (IIa) in a solvent (e.g., acetic acid, water or methanol) to obtain a sulfoxide (IIb) or a sulfone (IIc). When the oxidizing agent in an amount of 1 mol equivalent is allowed to react on the sulfide (IIa), the sulfoxide (IIb) is obtained. When the oxidizing agent in an amount of 2 mol equivalents is allowed to react on the sulfide (IIa), the sulfone (IIc) is obtained.

The herbicide of the present invention contains, as an active ingredient, the novel cyclohexanedione derivatives of the formula (I) or the salts thereof. These compounds can be used in any form of a wettable powder, an emulsifiable concentrate, a dust and granules prepared by mixing the cyclohexanedione derivatives or the salts thereof with a liquid carrier such as a solvent or a solid carrier such as a fine mineral powder. For imparting these compounds with emulsifiability, dispersibility and wettability in producing the above preparations, a surfactant can be added.

When the herbicide of the present invention is used in the form of a wettable powder, the wettable powder is generally prepared by mixing 10 to 55% by weight of the cyclohexanedione derivatives or the salts thereof, provided by the present invention, 40 to 88% by weight of a solid carrier and 2 to 5% by weight of a surfactant.

When the herbicide of the present invention is used in the form of an emulsifiable concentrate, it is generally prepared by mixing 20 to 50% by weight of the cyclohexanedione derivatives or the salts thereof, provided by the present invention, 35 to 75% by weight of a solvent and 5 to 15% by weight of a surfactant.

When the herbicide of the present invention is used in the form of dust, the dust is generally prepared by mixing 1 to 15% by weight of the cyclohexanedione derivatives or the salts thereof, provided by the present invention, 80 to 97% by weight of a solid carrier and 2 to 5% by weight of a surfactant.

When the herbicide of the present invention is used in the form of granules, the granules are generally prepared by mixing 1 to 15% by weight of the cyclohexanedione derivatives or the salts thereof, provided by the present invention, 80 to 97% by weight of a solid carrier and 2 to 5% by weight of a surfactant.

The above solid carrier is selected from oxides such as diatomaceous earth, slaked lime, phosphates, sulfates such as gypsum, and silicates such as talc, pyrophyllite, clay, kaolin, bentonite, acid clay, white carbon, powdered quartz and a silica powder.

The above solvent is selected from organic solvents, and specific examples of the organic solvents include aromatic hydrocarbons such as benzene, toluene and xylene, chlorinated hydrocarbons such as o-chlorotoluene, trichloromethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, dimethyl ether and methyl ethyl ether, esters such as isopropyl acetate, benzyl acetate and methyl fumarate, amides such as dimethylformamide, and mixtures of these.

Further, the above surfactant is selected from anionic surfactants, nonionic surfactants, cationic surfactants and amphoteric surfactants (amino acid and betaine).

The herbicide of the present invention is applied at such a rate that the amount of the cyclohexanedione derivative or its salt as an active ingredient is generally 1 g to 1,000 g per 10 are, preferably 5 g to 100 g.

The herbicide of the present invention may contain other herbicidally active component if necessary in combination with the cyclohexanedione derivatives of the general formula (I) or the salts thereof as active ingredients. This "other" herbicidally active component includes known herbicides such as phenoxy, diphenylether, triazine, urea, carbamate, thiolcarbamate, acid anilide, pyrazole, phosphoric acid, sulfonylurea and oxadiazon herbicides. This "other" herbicide is properly selected from these herbicides.

Further, the herbicide of the present invention may be used in combination with an insecticide, a fungicide, a plant growth regulator and a fertilizer if necessary.

The present invention will be explained further in detail with reference to Examples, while the present invention shall not be limited thereto.

REFERENTIAL EXAMPLE

4-Methoxyimino-5,8-dimethylthiochroman-6-carboxylic acid-1,1-dioxide, used as a starting material in Preparation Example to be described later, was produced as follows.

Step (1): 3.2 Grams (12 mmol) of 5,8-dimethyl-6 -bromothiochroman-4-one and 1.9 g (23 mmol) of O-methylhydroxylamine hydrochloride were refluxed in a solvent mixture of 10 ml of ethanol and 10 ml of pyridine under heat for 30 minutes. The solvent was distilled off under reduced pressure, and then 50 ml of 5% hydrochloric acid was added to form a solid. The solid was recovered by filtration, washed with water and dried to give 3.4 g of 4 -methoxyimino-5,8-dimethyl-6-bromothiochroman (yield 93%).

N.M.R. ($CDCl_3$, ppm): 2.28 (3H,s), 2.57 (3H,s), 2.7–3.3 (4H,m), 3.98 (3H,s), 7.55 (1H,s)

Step (2): 1.1 Grams (45 mmol) of magnesium was dispersed in 10 ml of THF (tetrahydrofuran), and 2.2 g (20 mmol) of ethyl bromide was added under nitrogen current. After the mixture was allowed to react for 10 minutes, a solution of 3.0 g (10 mmol) of the 4-methoxyimino-5,8 -dimethyl-6-bromothiochroman obtained in the above step (1) in THF was gradually added at room temperature. The reaction mixture was refluxed for 3 hours and cooled to room temperature, and carbon dioxide gas was bubbled for 1 hour. 20 Milliliters of 5% hydrochloric acid was added to the reaction mixture, and the mixture was extracted with diethyl ether. The ether layer was extracted with a 5% potassium carbonate aqueous solution, and the aqueous layer was neutralized with concentrated hydrochloric acid. The neutralized water layer was extracted with ethyl acetate, and the ethyl acetate layer was washed with a saturated sodium chloride aqueous solution. The ethyl acetate layer was dried over anhydrous sodium sulfate, and the solvent was distilled off to give 1.7 g of 4-methoxyimino-5,8 -dimethylthiochroman-6-carboxylic acid (yield 64%).

N.M.R. ($CDCl_3$, ppm): 2.32 (3H,s), 2.73 (3H,s), 2.7–3.3 (4H,m), 3.99 (3H,s), 7.75 (1H,s), 8.1 (1H,brs) I.R. (KBr tablet, $cm^{-1}$): 3,200–2,400, 1,690, 1,050.

Step (3): 1.0 Gram (3.8 mmol) of the 4 -methoxyimino-5,8-dimethylthiochroman-6-carboxylic acid obtained in the above step (2) was allowed to react with 1.3 g ( 12 mmol) of a 30% hydrogen peroxide aqueous solution in acetic acid at 100° C. for 1 hour. The reaction mixture was extracted by adding ethyl acetate, and the ethyl acetate layer was washed with a saturated sodium chloride aqueous solution and dried over anhydrous sodium sulfate. The solvent was distilled off to give 1.1 g of 4-methoxyimino- 5,8-dimethylthiochroman-6-carboxylic acid-1,1-dioxide (yield 97%).

N.M.R. ($CDCl_3$, ppm): 2.71 (3H,s), 2.75 (3H,s), 3.1–3.5 (4H,m), 4.05 (3H,s), 7.79 (1H,s), 8.5 (1H,brs) I.R. (KBr tablet, $cm^{-1}$): 3,400–2,500, 1,700, 1,330, 1,120. m.p.: 168.7°–170.7° C.

PREPARATION EXAMPLE 1

Synthesis of 4-methoxyimino-5,8-dimethyl-6-(1,3 -dioxycyclohex-2-yl)-carbonylthiochroman-1,1-dioxide (Compound No. 1)

0.7 Gram (2.4 mmol) of the 4-methoxyimino-5,8 -dimethylthiochroman-6-carboxylic acid-1,1-dioxide prepared in Referential Example and 0.28 g (2.5 mmol) of cyclohexane- 1,3-dione were mixed in 10 ml of acetonitrile, and 0.53 g (2.6 mmol) of DCC (dicyclohexylcarbodiimide) was added at room temperature. After 8 hours, 0.36 g (3.6 mmol) of triethylamine and 0.1 ml of acetonecyanohydrin were added to the reaction mixture, and the mixture was allowed to react for further 8 hours. The acetonitrile was distilled off., and then ethyl acetate and a 5% potassium carbonate aqueous solution were added. Insolubles were removed by filtration. The aqueous layer was neutralized with 5% hydrochloric acid, and the precipitate was recovered by filtration and dried to give 0.41 g of the intended product (Compound (1)) (yield 44%).

PREPARATION EXAMPLES 2 and 3

Compounds (2) and (3) were obtained in the same manner as in Preparation Example 1 except that 0.8 g (2.9 mmol) of 4-ethoxyimino-5,8-dimethylthiochroman-6-carboxylic acid and 0.7 g (2.3 mmol) of 4.-ethoxyimino-5,8 -dimethylthiochroman-6-carboxylic acid-1,1-dioxide were used as starting materials. Compound (2) and Compound (3) shown in the following Table 1 were obtained in amounts of 0.5 g (yield 45%) and 0.2 g (yield 21%), repectively.

PREPARATION EXAMPLES 4–6

Compounds (4), (5) and (6) were obtained while using 0.70 g (2.4 mmol) of 4-methoxyimino-5,8 -dimethylthiochroman-6-carboxylic acid-1,1-dioxide as a starting material except that the cyclohexane-1,3-dione was replaced with 0.35 g (2.5 mmol) of 5,5-dimethylcyclohexane- 1,3-dione (dimedone), 0.35 g (2.5 mmol) of 4,4-dimethylcyclohexane-1,3-dione and 0.39 g (2.5 mmol) of 5 -isopropylcyclohexane- 1,3-dione. Compounds (4), (5) and (6) shown in the following Table 2 were obtained in amounts of 0.24 g (yield 24%), 0.37 g (yield 37%) and 0.54 g (yield 52%), respectively.

PREPARATION EXAMPLE 7

Compound (7) was obtained in the same manner as in Preparation Example 1 except that 0.5 g of 4-isopropoxyimino-5,8-dimethylthiochroman-6-carboxylic acid-1,1-dioxide was used as a starting material. Compound (7) shown in the following Table 3 was obtained in an amount of 0.4 g (yield 62%).

PREPARATION EXAMPLE 8

Compound (8) was obtained in the same manner as in Preparation Example 1 except that 1.0 g of 4-methoxyimino-5-methylthiochroman-6-carboxylic acid-1,1-dioxide was used as a starting material. Compound (8) shown in the following Table 3 was obtained in an amount of 0.69 g (yield 51%).

PREPARATION EXAMPLE 9

Compound (9) was obtained in the same manner as in Preparation Example 1 except that 1.0 g of 4-methoxyimino-5-methylthiochroman-6-carboxylic acid-1,1 -dioxide and 0.54 g of 4,4-dimethylcyclohexane-1,3-dione were used as starting materials. Compound (9) shown in the following Table 3 was obtained in an amount of 0.78 g (yield 54%).

PREPARATION EXAMPLE 10

Compound (10) was obtained in the same manner as in Preparation Example 1 except that 1.3 g of 4-ethoxyimino-5-methylthiochroman-6-carboxylic acid-1,1-dioxide and 0.54 g of cyclohexane-1,3-dione were used as starting materials. Compound (10) shown in the following Table 4 was obtained in an amount of 0.95 g (yield 55%).

PREPARATION EXAMPLE 11

Compound (11) was obtained in the same manner as in Preparation Example 1 except that 1.3 g of 4-ethoxyimino-5-methylthiochroman-6-carboxylic acid-1,1-dioxide and 0.67 g of 4,4-dimethylcyclohexane-1,3-dione were used as starting materials. Compound (11) shown in the following Table 4 was obtained in an amount of 0.35 g (yield 19%).

PREPARATION EXAMPLE 12

Compound (12) was obtained in the same manner as in Preparation Example 1 except that 1.0 g of 4-ethoxyimino-5,8-dimethylthiochroman-6-carboxylic acid-1,1-dioxide and 0.50 g of 4,4-dimethylcyclohexane-1,3-dione were used as starting materials. Compound (12) shown in the following Table 4 was obtained in an amount of 0.22 g (yield 16%).

Tables 1 to 4 shows the compounds of the present invention obtained in the above Examples.

TABLE 1

| Compound No. | Structural Formula | Infrared Absorption Spectrum KBr Tablet (cm$^{-1}$) | Proton Magnetic Resonace Spectrum (ppm) | mp (°C.) |
| --- | --- | --- | --- | --- |
| (1) | [structure] | 3450, 2960, 1680, 1320, 1130 | 1.8–2.3(2H, m), 2.35(3H, s), 2.3–2.9(4H, m), 2.69(3H, s), 3.2–3.6(4H, m), 4.00(3H, s), 6.91(1H, s) (CDCl$_3$) | 219.3–222.8 |
| (2) | [structure] | 3450, 2990, 1680, 1050 | 1.34(3H, 1), 1.8–2.8(6H, m), 2.32(3H, s), 2.50(3H, s), 2.8–3.2(4H, m), 4.23(2H, q), 6.87(1H, s) (CDCl$_3$) | — |

TABLE 1-continued

| Compound No. | Structural Formula | Infrared Absorption Spectrum KBr Tablet (cm⁻¹) | Proton Magnetic Resonace Spectrum (ppm) | mp (°C.) |
|---|---|---|---|---|
| (3) | [structure with cyclohexanedione, benzene ring with CH₃ groups, NOC₂H₅ oxime, SO₂ thiopyran] | 3460 2990 1680 1310 1120 | 1.31(3H, t), 1.9–2.3(2H, m) 2.35(3H, s), 2.47(2H, t) 2.70(3H, s), 2.80(2H, t) 3.2–3.6(4H, m), 4.26(2H, q) 6.91(1H, s) (CDCl₃) | 171.0–171.9 |

TABLE 2

| Compound No. | Structural Formula | Infrared Absorption Spectrum KBr Tablet (cm⁻¹) | Proton Magnetic Resonace Spectrum (ppm) | mp (°C.) |
|---|---|---|---|---|
| (4) | [structure with 5,5-dimethylcyclohexanedione, benzene ring with CH₃ groups, NOCH₃ oxime, SO₂ thiopyran] | 3500 1680 1320 1060 | 1.12(6H, s), 1.8(1H, brs), 2.1–2.9(4H, m) 2.22(3H, s), 2.68(3H, s), 3.2–3.5(4H, m) 4.01(3H, s), 6.91(1H, s) (CDCl₃) | — |
| (5) | [structure with 4,4-dimethylcyclohexanedione, benzene ring with CH₃ groups, NOCH₃ oxime, SO₂ thiopyran] | 3450 2990 1680 1050 | 1.12(3H, s), 1.3–1.7(3H, m), 1.88(2H, t) 3.3–3.0(2H, m), 2.33(3H, s), 2.68(3H, s) 3.2–3.5(4H, m), 4.01(3H, s), 6.88(1H, s) (CDCl₃) | 219.3–222.8 |
| (6) | [structure with isopropyl-cyclohexanedione, benzene ring with CH₃ groups, NOCH₃ oxime, SO₂ thiopyran] | 3460 2990 1680 1310 1120 | 0.93(6H, d), 1.9–2.8(6H, m), 2.31(3H, s) 2.62(3H, s), 3.1–3.6(4H, m), 7.03(1H, s) (d-acetone) | — |

TABLE 3

| Compound No. | Structural Formula | Infrared Absorption Spectrum KBr Tablet (cm⁻¹) | Proton Magnetic Resonace Spectrum (ppm) | mp (°C.) |
|---|---|---|---|---|
| (7) | [structure with cyclohexanedione, benzene ring with CH₃ groups, NOCH(CH₃)₂ oxime, SO₂ thiopyran] | 3450 1960 1320 1110 | 1.29(6H, d), 1.9–2.3(2H, m), 2.35(3H, s) 2.4–2.6(2H, m), 2.69(3H, s), 2.7–3.0(2H, m) 3.2–3.5(4H, m), 4.45(1H, m), 6.90(1H, s) (CDCl₃) | 164.7–166.9 |

TABLE 3-continued

| Compound No. | Structural Formula | Infrared Absorption Spectrum KBr Tablet (cm$^{-1}$) | Proton Magnetic Resonace Spectrum (ppm) | mp (°C.) |
|---|---|---|---|---|
| (8) | [structure with cyclohexanedione, CH$_3$, NOCH$_3$, SO$_2$ groups] | 3450 1680 1320 1130 | 1.9–2.3(2H, m), 2.3–2.6(2H, m), 2.43(3H, s) 2.7–3.0(2H, m), 3.3–3.4(4H, m) 4.04(3H, s), 7.62(2H, ABq) (CDCl$_3$) | 153.1–162.6 |
| (9) | [structure with dimethyl cyclohexanedione, CH$_3$, NOCH$_3$, SO$_2$ groups] | 3450 1740 1680 1330 1130 | 1.0–1.6(6H, m), 1.7–2.0(2H, m), 2.3–2.9(5H, m) 3.2–3.5(4H, m), 4.04(3H, s), 7.1–8.0(2H, m) (CDCl$_3$) | gum |

TABLE 4

| Compound No. | Structural Formula | Infrared Absorption Spectrum KBr Tablet (cm$^{-1}$) | Proton Magnetic Resonace Spectrum (ppm) | mp (°C.) |
|---|---|---|---|---|
| (10) | [structure with cyclohexanedione, CH$_3$, NOC$_2$H$_5$, SO$_2$ groups] | 3500 1680 1320 1130 | 1.33(3H, t), 1.9–2.3(2H, m), 2.3–2.6(2H, m) 2.44(3H, s), 2.44(3H, s), 2.7–3.0(2H, m) 3.2–3.5(4H, m), 4.28(2H, q), 7.62(2H, ABq) (CDCl$_3$) | 175.6–178.9 |
| (11) | [structure with dimethyl cyclohexanedione, CH$_3$, NOC$_2$H$_5$, SO$_2$ groups] | 3500 1690 1330 1110 | 1.1–1.5(6H, m), 1.29(3H, t), 1.88(2H, m) 2.42(3H, s), 2.5–3.0(2H, m)4.30(2H, q) 7.0–8.0(2H, m) (CDCl$_3$) | glassy matter |
| (12) | [structure with dimethyl cyclohexanedione, CH$_3$, NOC$_2$H$_5$, SO$_2$, CH$_3$ groups] | — | 1.1–1.7(6H, m), 1.31(3H, t), 1.88(2H, t), 2.33(3H, s)2.50(1H, t), 2.69(3H, s)2.81(1H, t) 3.2–3.5(4H, m), 4.26(2H, q), 6.87(1H, s) (CDCl$_3$) | 145.4–149.5 |

HERBICIDE EXAMPLE (1) Preparation of Herbicide

A carrier for a wettable powder was prepared by uniformly pulverizing and mixing 97 parts by weight of talc (trade name: Zeaklite, supplied by Zeaklite Kogyo K.K.), 1.5 parts by weight of alkylarylsulfonic acid (trade name: Neoplex, supplied by Kao-Atlas K.K. ) as a surfactant and 1.5 parts by weight of a nonionic and anionic surfactant (trade name: Sorpol 800A, supplied by Toho Chemical Co., Ltd.).

90 Parts by weight of the above carrier for a wettable powder and 10 parts by weight of one of the compounds of the present invention obtained in the above Preparation Examples were uniformly pulverized and mixed to obtain a herbicide. For comparison, 90 parts by weight of the above carrier for a wettable powder and 10 parts by weight of one of the following compounds (A) to (E) were uniformly pulverized and mixed to obtain a herbicide.

The compound (A) used for comparison is Compound No. 51 described in JP-B-1-30818 and has the following structure.

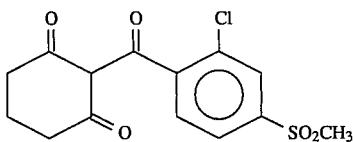

Compound No. 51

The compound (B) used for comparison is described in JP-A-61-155347 and has the following structure.

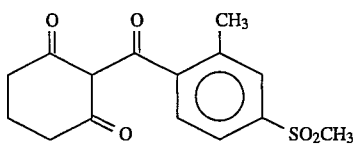

The compounds (C), (D) and (E) are described JP-A-64-6256 and have the following structures.

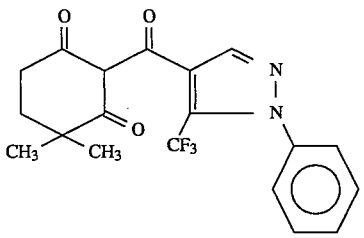

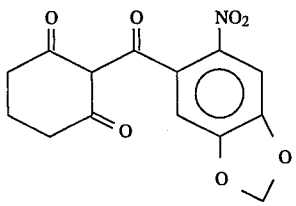

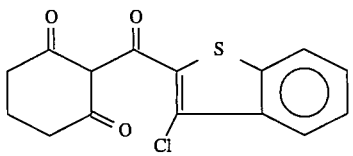

(2) Test on Foliar Treatment

Seeds of weeds such as barnyardgrass, green foxtail, cocklebur, velvetleaf and slender amaranth, and seeds of corn, wheat and barley were sown in 1/5,000 are Wagner pots filled with upland soil, and covered with upland soil. Then, the seeds were grown in a greenhouse, and at the one or two-leaved stage of these plants, the herbicides obtained in the above (1) were suspended in water and uniformly sprayed to foliar portions at a rate of 200 liter/10 ares (dosage 32 g/10 ares). Thereafter the plants were grown in the greenhouse, and 20 days after the spray treatment, the herbicides were determined for herbicidal efficacy and phytotoxicity to the crops. Tables 5 and 6 show the results.

The herbicidal efficacy and the phytotoxicity to the crops are shown on the basis of the following ratings.

| (Ratings) | Remaining plant weight/ non-treated ratio [%] |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity | |
| – | 100 |
| ± | 95–99 |
| + | 90–94 |
| ++ | 80–89 |
| +++ | 0–79 |

The remaining plant weight/non-treated ratio was calculated by the following equation.

Remaining plant weight/non-treated ratio [%]=(remaining plant weight in treated area/remaining plant weight in non-treated area)×100.

TABLE 5

| Test Compound No. | Dosage g a.i./a | Herbicidal efficacy | | | | | Phytotoxicity | | |
|---|---|---|---|---|---|---|---|---|---|
| | | Barnyard-grass | Green foxtail | Cockle-bur | Velvet leaf | Slender amaranth | Corn | Wheat | Barley |
| (1) | 3.2 | 5 | 5 | 5 | 5 | 5 | – | – | – |
| (2) | 3.2 | 4 | 2 | 5 | 5 | 4 | – | – | – |
| (3) | 3.2 | 5 | 5 | 5 | 5 | 5 | – | – | – |
| (4) | 3.2 | 5 | 5 | 5 | 5 | 5 | – | – | – |
| (5) | 3.2 | 5 | 5 | 5 | 5 | 5 | – | – | – |
| (6) | 3.2 | 5 | 5 | 5 | 5 | 5 | – | – | – |
| (7) | 3.2 | 3 | 1 | 5 | 5 | 3 | – | – | – |
| (8) | 3.2 | 5 | 5 | 5 | 5 | 5 | – | – | – |
| (A) | 3.2 | 0 | 0 | 4 | 4 | 2 | – | – | – | a.i. = abbreviation for active ingredient

TABLE 6

| Test Compound No. | Dosage g a.i./a | Herbicidal efficacy | | | | | Phytotoxicity | | |
|---|---|---|---|---|---|---|---|---|---|
| | | Barnyard-grass | Green foxtail | Cockle-bur | Velvet leaf | Slender amaranth | Corn | Wheat | Barley |
| (9) | 3.2 | 5 | 4 | 5 | 5 | 5 | ± | — | — |
| (10) | 3.2 | 5 | 4 | 5 | 5 | 5 | — | — | — |
| (11) | 3.2 | 5 | 5 | 5 | 5 | 4 | ± | — | — |
| (12) | 3.2 | 5 | 3 | 5 | 5 | 4 | ± | — | — |
| (A) | 3.2 | 0 | 0 | 4 | 4 | 2 | — | — | — |
| (B) | 3.2 | 0 | 0 | 4 | 4 | 1 | — | — | — |
| (C) | 3.2 | 1 | 0 | 3 | 2 | 1 | — | — | — |
| (D) | 3.2 | 0 | 1 | 3 | 3 | 2 | — | — | — |
| (E) | 3.2 | 0 | 0 | 2 | 2 | 1 | — | — | — | a.i. = abbreviation for active ingredient

Tables 5 and 6 clearly show that herbicides containing the cyclohexanedione derivatives, provided by the present invention, have no phytotoxicity to corn, wheat and barley and exhibit excellent herbicidal effects on gramineous weeds (barnyardgrass and green foxtail) and broad-leaved weeds (cocklebur, velvetleaf and slender amaranth) at low dosage. In contrast, herbicides containing the known cyclohexanedione derivatives (A) to (E) showed poor herbicidal activity to barnyardgrass, green foxtail and slender amaranth and did not have a sufficient herbicidal effect.

As described above, the present invention provides novel cyclohexanedione derivatives or salts thereof which exhibit high selectivity for corn, wheat and barley and can control gramineous weeds and broad-leaved weeds at a low dosage; and herbicides containing the above cyclohexanedione derivatives and/or salts thereof as active ingredients.

What is claimed is:

1. A cyclohexanedione compound of the formula (I),

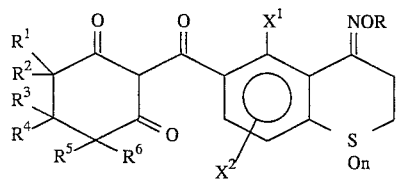

wherein:

R is a $C_1$-$C_4$ alkyl group, each of $R^1$ to $R^6$ is independently hydrogen or a $C_1$-$C_4$ alkyl group, $X^1$ is a $C_1$-$C_4$ alkyl group, $X^2$ is hydrogen or a $C_1$-$C_4$ alkyl group, and n is an integer of 0 to 2, or a salt thereof.

2. A herbicidal composition comprising a herbicidal effective amount of the cyclohexanedione compound of the formula (I) or a salt thereof according to claim 1 and a liquid or a solid carrier.

3. The cyclohexanedione compound or salt thereof according to claim 1, wherein R is methyl or ethyl.

4. The cyclohexanedione compound or salt thereof according to claim 1, wherein each of $R^1$ to $R^6$ is independently hydrogen or methyl.

5. The cyclohexanedione compound or salt thereof according to claim 1, wherein $X^1$ is methyl.

6. The cyclohexanedione compound or salt thereof according to claim 1, wherein $X^2$ is hydrogen or methyl.

7. The cyclohexanedione compound or salt thereof according to claim 1, wherein $X^2$ is substituted on the 7- or 8-position of the thiochroman ring.

8. The cyclohexanedione compound or salt thereof according to claim 1, wherein n is 2.

9. The cyclohexanedione compound or salt thereof according to claim 1, wherein R is methyl or ethyl, each of $R^1$ to $R^6$ is independently hydrogen or methyl, $X^1$ is methyl, $X^2$ is hydrogen or methyl and is substituted on the 7- or 8-position of the thiochroman ring, and n is 2.

10. The cyclohexanedione compound or salt thereof according to claim 1, wherein the compound is selected from the group consisting of

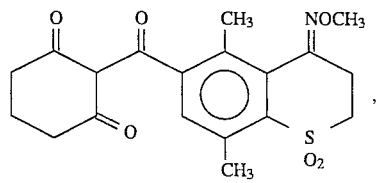

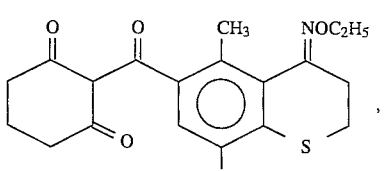

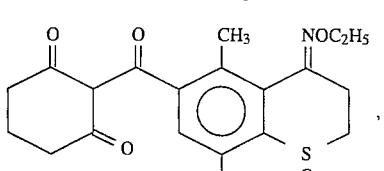

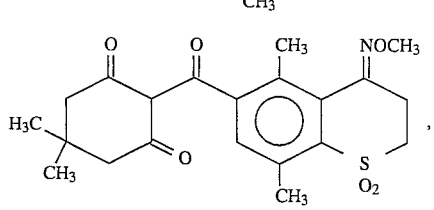

-continued
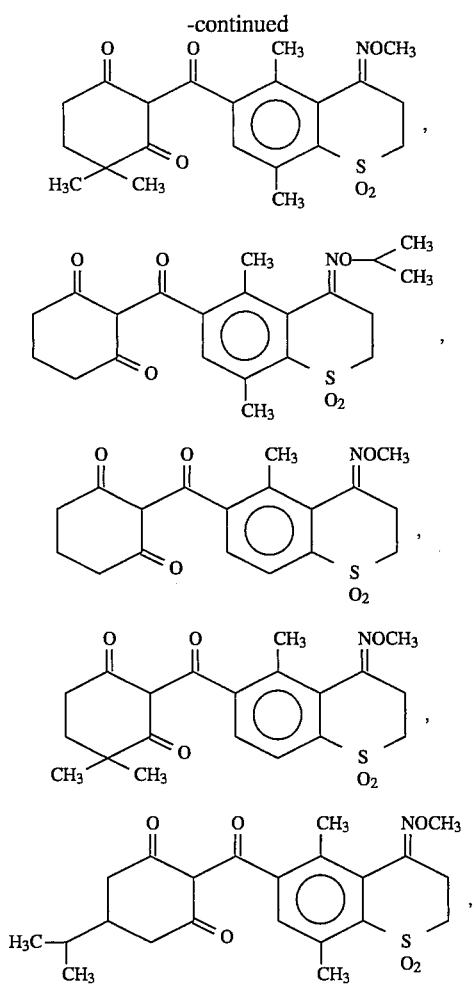
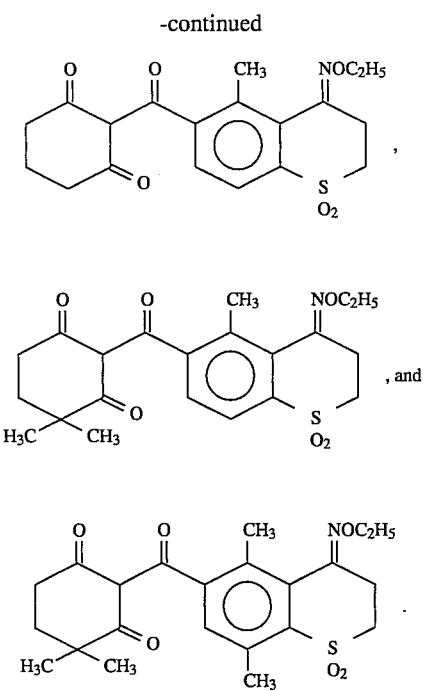
11. A method of combatting weeds by applying to weeds or a locus thereof, an effective herbicidal amount of the cyclohexanedione compound or salt thereof according to claim 1.
* * * * *